(12) United States Patent
Mthethwa (10) Patent No.: US 10,925,989 B1
(45) Date of Patent: Feb. 23, 2021

(54) SANITIZATION BOOTH

(71) Applicant: Wiseman Dumisani Mthethwa, Umhlanga Rocks (ZA)

(72) Inventor: Wiseman Dumisani Mthethwa, Umhlanga Rocks (ZA)

(73) Assignee: Wiseman Dumisani Mthethwa, Umhlanga Rocks (ZA)

( * ) Notice: Subject to any disclaimer, the term of this patent is extended or adjusted under 35 U.S.C. 154(b) by 0 days.

(21) Appl. No.: 16/884,739

(22) Filed: May 27, 2020

(30) Foreign Application Priority Data

Apr. 7, 2020 (AU) .................................. 2020901083

(51) Int. Cl.
*A61L 2/22* (2006.01)
*B05B 14/40* (2018.01)

(52) U.S. Cl.
CPC ................ *A61L 2/22* (2013.01); *B05B 14/40* (2018.02); *A61L 2202/121* (2013.01); *A61L 2202/122* (2013.01); *A61L 2202/14* (2013.01); *A61L 2202/15* (2013.01); *A61L 2202/16* (2013.01); *A61L 2202/26* (2013.01)

(58) Field of Classification Search
CPC .... A61L 2/22; A61L 2202/26; A61L 2202/16; A61L 2202/122; A61L 2202/121; A61L 2202/15; A61L 2202/14; B05B 14/40
See application file for complete search history.

(56) References Cited

U.S. PATENT DOCUMENTS

| | | | | |
|---|---|---|---|---|
| 3,576,206 A | * | 4/1971 | Trexler | E06B 7/28 160/84.02 |
| 4,279,263 A | * | 7/1981 | Pulliam | B60S 3/044 134/111 |
| 4,675,923 A | * | 6/1987 | Ashley | A47K 3/286 4/596 |
| 2006/0258279 A1 | * | 11/2006 | Bonnard | A61L 2/18 454/55 |
| 2017/0173200 A1 | * | 6/2017 | Wyman | A61L 2/0088 |

* cited by examiner

*Primary Examiner* — Sean E Conley
*Assistant Examiner* — Brendan A Hensel
(74) *Attorney, Agent, or Firm* — M&B IP Analysts, LLC (57) ABSTRACT

The invention provides a sanitization booth 10 has side walls 12 approximately twice as long as it's entrance and exit openings 14, 16 are wide to permit a person to step into the booth and pass therethrough while being sprayed or misted with a sanitization or disinfection liquid, from above 18, below 20, and the sides 22 by liquid sanitizer pumped through a reticulation pipe system 24 and through nozzles 26 along the extent thereof, thereby to sanitize the person, their clothing, as well as their footwear including the soles thereof. The booth 10 includes a hand sanitization point 28 at the entrance 14 to the booth 10 so that the person who has been sanitized by passing through the booth also sanitizes their hands which have been used to cover their eyes while in the booth. The invention also provides a sanitization system and a kit for assembly of a sanitization apparatus.

18 Claims, 11 Drawing Sheets

SANITIZATION BOOTH

CROSS-REFERENCE TO RELATED APPLICATIONS

This application claims the benefit of Australian Provisional Patent Application 2020901083, filed Apr. 7, 2020, all contents of which are hereby incorporated by reference.

TECHNICAL FIELD

The invention is in the field of sanitization of persons, their property, and in particular their clothing. The invention provides a sanitization apparatus for this purpose.

BACKGROUND

Although this patent application is being filed at a time of COVID-19 pandemic where hand sanitization is widely recommended as are other measures to prevent the transmission of the disease from person to person, the inventor is aware of an ongoing need for the sanitization of persons and their property, particularly when entering premises which may be contaminated by a person who has a pathogen on their exposed body parts or clothing, who is visibly ill, or who displays common symptoms of contagious illnesses such as fever.

The inventor is aware of various sanitization systems which are multistage i.e. requiring the separate sanitization by use of different spaced apart equipment of the hands, boots and clothing of a person, such as those found in food processing plants. These systems are designed for use in specific areas of food processing and such similar facilities by persons trained for their use and rely on the person changing into clean sanitized clothing just prior to entering the facility and then using the equipment to clean their hands and sanitize them while a boot scrubber and sanitizer scrubs and sanitizes the boots. Typically, the user would also wear disposable personal protective gear for covering hair, beards etc. to reduce the risk of contamination.

The above described system clearly cannot be used for the general population or at access points for the public or general employees onto a premises which is not geared for such a high level of hygiene. The inventor has thus considered this problem and proposes the invention described herebelow.

SUMMARY

According to a first aspect of the invention, there is provided a sanitization apparatus which includes:— a framework which defines a sanitizing zone shaped and dimensioned to permit a person to pass therethrough while being sprayed with a sanitizer;

sprayers arranged on the framework for spraying a sanitizer into the sanitizing zone to allow substantial sanitization of an outer surface of a person including his clothing, footwear and the soles of the footwear; and a flow communication means for allowing flow communication between the sprayers and a supply of sanitizer via a fluid displacement means.

The framework may be in the form of a doorway which may be free standing or operatively associated with a door frame so that a person passing through the doorframe may be sanitized.

The apparatus may be in the form of a kit for retrofitting to an existing doorway frame.

The sprayers may include nozzles located to spray the footwear of the person including the soles thereof. The nozzles may be located over a major portion of the framework so that they spray inwardly onto the person passing through the sanitizing zone from above, sides and from below thereby to allow a mist of sanitizer and/or disinfectant to be deposited onto an outer surface of a person including his clothing, footwear and the soles of the footwear almost entirely or entirely. The nozzles may be configured to atomize the sanitizer upon spraying thereof into the sanitization zone.

For the purposes of this specification, the term sanitizer shall be understood as to include but not be limited to any sanitizer, disinfectant and/or sterilizing agent for use in safely sanitizing an outer surface of a person.

The framework may be in the form of a booth having an entrance and an exit, whereby a person enters into the booth, remains in the booth to be sprayed or misted, and then exits the booth.

The apparatus may include a hand sanitization portion which is arranged in flow communication with the supply of sanitizer. The hand sanitizer portion may be directed away from the framework in the direction of the person as they approach or depart so as to facilitate sanitization of the person's hands which may have been used to cover their eyes as they passed through the sanitization zone.

The booth may include a hand sanitization portion which is arranged in flow communication with the supply of sanitizer. The hand sanitization portion may be located at an entrance and/or an exit of the booth so as to facilitate sanitization of the person's hands which may have been used to cover their eyes while in the booth.

The booth may have two or more side walls and a substantially perforated, latticed and/or foraminous floor for allowing a sanitizer mist sprayed toward the person from below to pass through the floor to sanitize the soles of the footwear of the person, while also permitting drainage of sprayed sanitizer from the booth. The floor may be made of grating, optionally having a drip tray arranged therebelow so as to contain any contaminated sanitizer and/or disinfectant after use. The drip tray may have a drain plug.

The booth may include a roof or ceiling wall extending between and interconnecting the side walls so as to form the entrance and exit and while allowing stray sanitizer to remain within the sanitization zone while fluid is being sprayed onto a person. It is to be appreciated that the roof and side walls inhibit upward and lateral displacement of sanitizer out of the booth in use.

The side walls and roof or ceiling may be made from a webbing material, such as canvas, nylon, polyester or the like. However, the side walls may be made of galvanized steel or stainless-steel sheeting, although it can be made of any suitable material.

The communication means may be in the form of a liquid reticulation system, typically including a network of pipes extending from the supply of sanitizer to and around the sanitization zone. The sprayers or nozzles may be mounted on the network of pipes at spaced apart intervals. Typically, the network of pipes may define an upper zone for spraying a person from above, a lower zone for spraying a person from below and an intermediate zone for spraying either or both side regions of a person passing through the sanitization zone.

A portion of the intermediate zone of the network of pipes may extend substantially parallel the direction of passage of a person passing through the sanitization zone.

The hand sanitization portion may be an extension of the intermediate zone of the network of pipes.

The upper zone of the liquid reticulation system may extend substantially around the periphery of an upper portion of the booth so that sanitizer may be sprayed on a person within the sanitization zone directly from above and angularly from above to improve coverage of the sanitizer being sprayed.

The upper zone of the liquid reticulation system may be substantially C-shaped, O-shaped or rectangular in configuration.

The lower zone of the liquid reticulation system may extend transversely and/or longitudinally the floor of the booth. However, the lower zone of the liquid reticulation system may extend substantially around the periphery of a lower portion of the booth so that the spray or mist is directed upwardly at the person in the booth as well as angularly from below to improve coverage by the sanitizer or disinfectant being sprayed onto the footwear and lower extremities of the person within the sanitization zone.

The supply of sanitizer may include a liquid container for sanitizer and/or disinfectant, and a container support portion whereby the liquid container is in a predetermined position relative to the orientation of the booth.

The fluid displacement means may be in the form of a pump which may be located on the framework in flow communication with an outlet of the container, an outlet of the pump being connected to the liquid reticulation system to supply the liquid reticulation system with pressurized liquid sanitizer from the container.

The apparatus may include consumption monitoring means for monitoring consumption of the sanitizer so as to allow a pre-determinable quantity of sanitizer to be sprayed onto a person.

The pump may be in the form of a dosing pump for allowing a pre-determinable quantity of sanitizer to be sprayed onto a person thereby to permit monitoring of a safe usage rate and consumption of the sanitizer. The dosing pump usage may be recorded.

The framework may include a flow meter whereby the amount of sanitizer passing through the sprayers or nozzles may be recorded for control purposes.

The liquid container may include level monitoring whereby the change in level of the sanitizer may be monitored and recorded.

The dosing pump usage, the flow meter readings, and/or the liquid container level monitoring may be reconciled as a measure of efficacy of the booth.

The apparatus may have a motion sensor whereby the pump, and thus the spray or mist, is started and stopped as the person passes into and out of the booth.

The framework and/or booth may be mobile with castors provided on a base thereof to permit relocation thereof.

According to a second aspect of the invention, there is provided a sanitization apparatus of the type described above, said apparatus including a symptom monitoring and access control system for checking persons prior to passing therethrough, when passing therethrough, or when exiting for common symptoms of contagious diseases and alarming when one or more symptoms are identified.

The symptom monitoring system may include a body temperature measurement system which either presents the temperature of the person to an operator or, through pre-programmed software, alarms when the person's temperature is outside predetermined parameters. The temperature measurement system may include an IR thermometer.

The symptom monitoring system may include a camera and software pre-programmed to identify common symptoms from the camera image, which may include thermal imaging. Where symptoms are identified from the camera image, the operator may be alerted and/or the alarm may be activated.

The symptoms which may be identified from a camera image may include, but are not limited to symptoms visible from eyes, skin color, sweat, coughing, and facial expression.

The booth may include access control whereby the person exhibiting symptoms is either prevented from passing through the booth, or where they have passed through the booth already, are prevented from entering the property until the operator has considered the situation and made a decision.

According to a third aspect of the invention, there is provided a system for sanitization of persons by means of a sanitizer or disinfectant spray or mist from several directions including at least from above and below thereby to sanitize the footwear of the person including the sole thereof, said system including a symptom monitoring and, optionally, an access control system for checking persons entering the booth for common symptoms of contagious diseases and alarming when one or more symptoms are identified.

The system may include spraying or misting the person from the sides, above, and below, as well as sanitizing the hands of the person prior to or upon exit from the system.

The symptom monitoring system may include a body temperature measurement which either presents the temperature of the person to an operator or, through pre-programmed software, alarms when the person's temperature is outside predetermined parameters.

The symptom monitoring system may include a camera and software pre-programmed to identify common symptoms from the camera image, which may include thermal imaging. Where symptoms are identified from the camera image the operator may be alerted and/or the alarm may be activated.

The symptoms which may be identified from the camera image may include, but are not limited to symptoms visible from eyes, skin color, sweat, coughing, and facial expression.

The system may include access control whereby the person exhibiting symptoms is prevented from entering a property until the operator has considered the situation and made a decision.

The system may include a motion sensor for control of the spray or mist.

The system may send a control signal to an automated access control turnstile or gate to allow or prevent access of the person.

According to a further aspect of the invention, there is provided a kit for assembly of an apparatus as hereinbefore described, the kit including:

reticulation piping pre-manufactured in sections and pre-bent to match a framework to which it is to be attached and to facilitate assembly of the reticulation piping; and framework components which have a sleeve and shaft weldless assembly mechanism having apertures through the sleeve and the shaft which apertures are in register for securing in position by one or more securing means selected from bolts, detent pins, and spring pressed detents thereby to facilitate assembly of the framework components for assembly of the framework.

BRIEF DESCRIPTION OF THE DRAWINGS

The invention will now be described, by way of a non-limiting example only, with reference to the accompanying drawings.

In the Figures.

DETAILED DESCRIPTION

Figure 1:
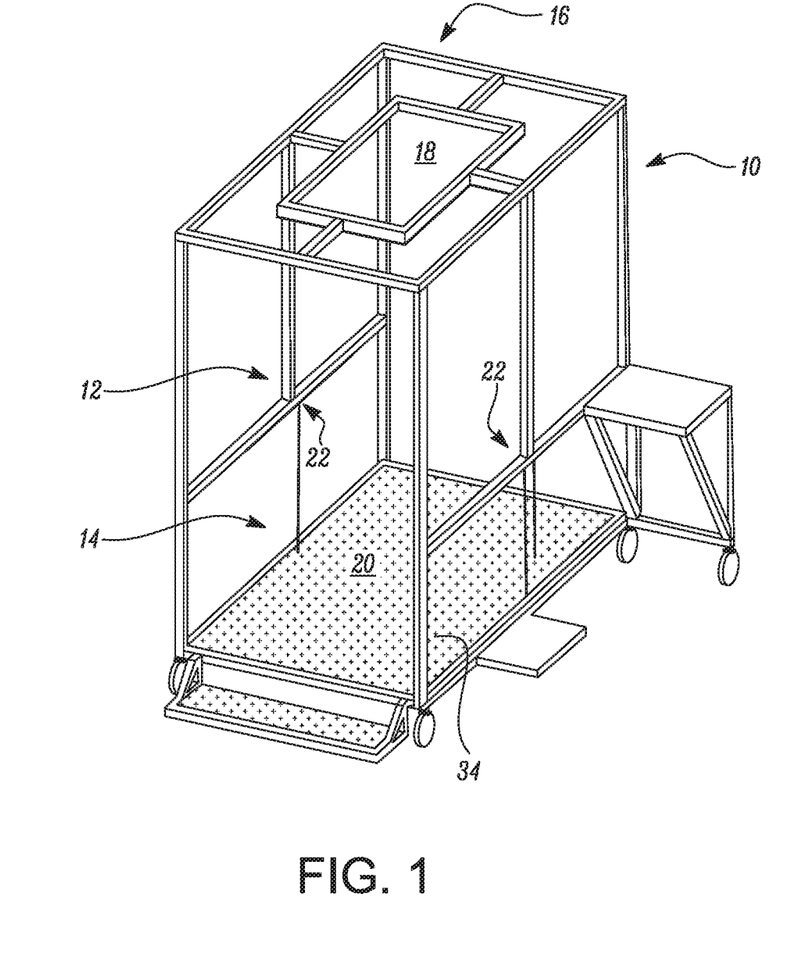
FIG. 1 shows an example of a booth of the invention, also referred to as a detection and sanitization station, with the sheeting removed to show the interior thereof.
Figure 2:
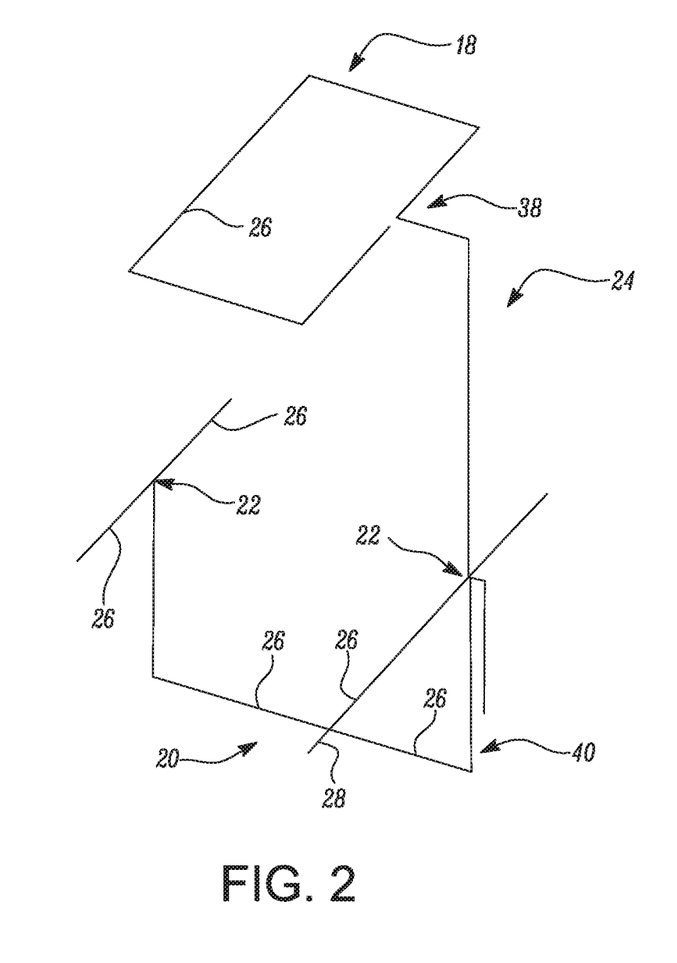
FIG. 2 shows a reticulation diagram for the booth of FIG. 1.
Figure 3:
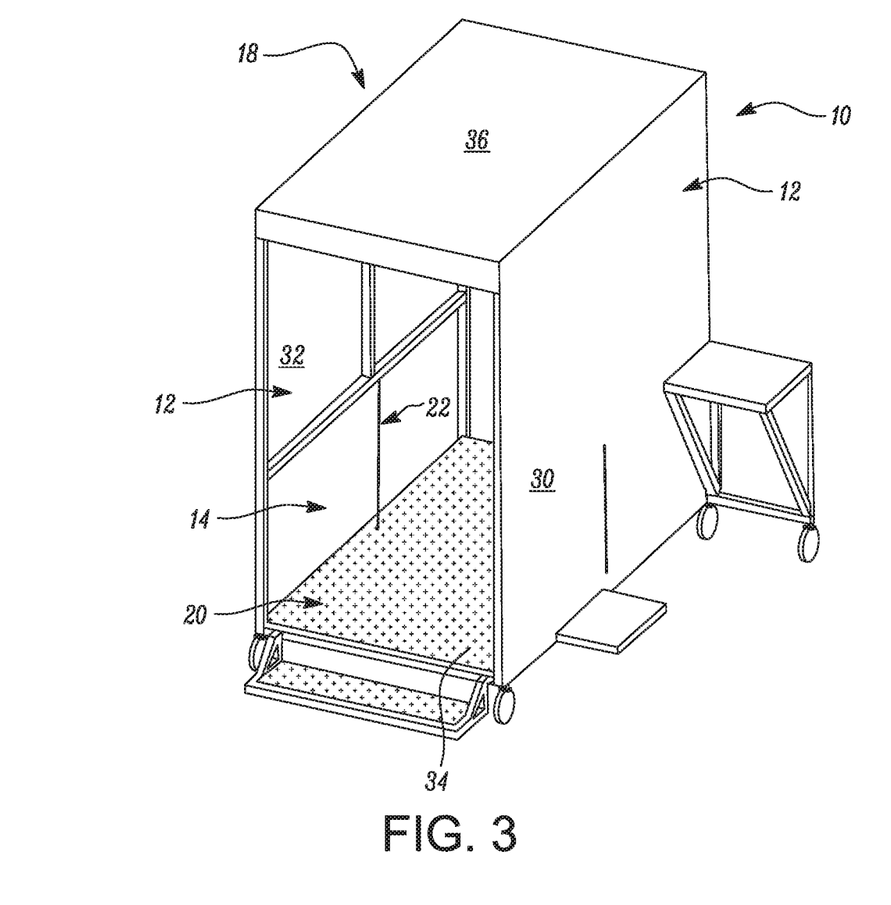
FIG. 3 shows the booth of FIG. 1 with sheeting covering the sides and roof thereof.

In FIGS. 1 to 3, a framework in the form of a sanitization booth 10 has side walls 12 approximately twice as long as it's entrance and exit openings 14, 16 are wide to permit a person to step into the booth and pass therethrough while being sprayed or misted with a sanitization or disinfection liquid, from above 18, below 20, and the sides 22 by liquid sanitizer pumped through a reticulation pipe system 24 and through nozzles 26 along the extent thereof, thereby to sanitize the person, their clothing, as well as their footwear including the soles thereof.

The booth 10 includes a hand sanitization portion 28 at the entrance 14 to the booth 10 so that the person who has been sanitized by passing through the booth also sanitizes their hands which have been used to cover their eyes while in the booth.

The booth 10 has side walls 30, 32 made from stainless sheeting and a grated floor 34 whereby the mist or spray directed at the person from below 20 passes through the floor to wet the soles of the footwear of the person, while also permitting drainage of the booth.

The booth also includes a roof or ceiling 36 also made from the same sheeting so that the booth 10 has two open ends, the entrance and exit openings 14, 16 for the person to enter and exit the booth while preventing the spray or mist from being distributed laterally and upwardly out of the booth.

An upper zone 38 of the liquid reticulation system 24 extends substantially around the periphery of an upper portion of the booth 10, in 0 or rectangular-fashion, so that the spray or mist is directed at the person in the booth from above as well as angularly from above to improve coverage by the liquid. Likewise, the lower zone 40 of the liquid reticulation system 24 extends transversely the floor 34 of the booth 10.

Figure 4:
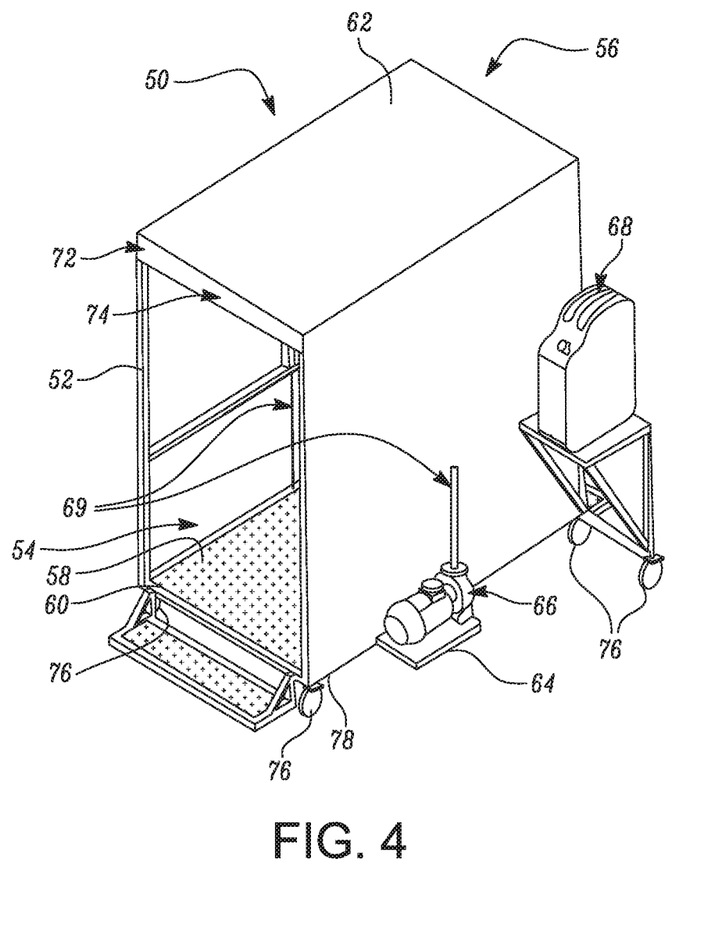
FIG. 4 shows an example of a booth of FIG. 1 including a liquid container and a pump.

In FIG. 4, in an embodiment of the invention, a booth 50 (detection & sanitization station) has a steel frame 52 passageway, with open ends 54, 56 for person/s to step into, walk through and exit on the opposite end. The booth 50 has a floor 58 which comprises of non-slip grating seated in a steel drip tray/catchment area 60. The frame 52 has sheeting 62 all round except for the entrance 54 and exit 56. On the right is a sub-frame 64 to support a 220V electric motor and pump system 66 with a liquid container 68 (header tank) mounted in flow communication and higher than an inlet of the pump 66.

The pump 66 is connected to and feeds a piping reticulation system 69 which distributes sanitization liquid solution from the container 68 to mist sprayers 70 which are distributed along the piping 69 above, along the sides and from below to achieve a 360 degree coverage and distribution of the liquid over the person/s inside the booth.

An infra-red camera 72 is mounted on the entrance 54 of the booth and is connected to a set of green, amber and red indication lights (not shown) and wired to a control box mounted on the frame (not shown).

A motion sensor 74 is mounted on the ceiling of the frame 52 to detect when a person/s have entered the booth.

A flow meter (not shown) will be mounted to the pump 66 to record volume dispensed for control of efficacy of the booth.

The booth has 5× lockable wheels 76 mounted on the corners of the base 78 and one supporting the sub frame 80.

Thus, in use, a person/s will stand at the entrance of the "detection & sanitization station" booth and during scanning or standby the amber indication light will be illuminated. Once scanned, if the temperature detected is higher than the upper pre-set limit, the red indication light will be illuminated as an alarm and the person/s will be asked to step aside for further examination. If cleared, the green indication light will illuminate allowing the person/s to enter for sanitization at entrance 54. The motion of the person entering the booth will trigger the motion sensor 74 mounted on the ceiling of the station which will toggle the electric motor to "ON", driving the pump 66 which will begin distributing the sanitization liquid solution for a pre-set time period to adequately sanitize the person/s inside the unit, once the run cycle is complete the motor will automatically switch off and the person/s can leave the station.

In order to ensure that there is no manipulation of the quality of the sanitizer or disinfectant, the container 68 is sealed and locked and the key kept by a responsible person to reduce the risk of tampering.

The outflow from the container 68 will be monitored through a flow meter to ensure that the sanitizer or disinfectant is correctly fed to the pump 66. The pump may be a dosing type pump. This is good for quality assurance as only the approved pre-mixed sanitizer or disinfectant will be utilized and records are kept and verified between the flow meter and the quantities supplied by the supplier. This will then allow for effective analysis of the amount of sanitizer or disinfectant used per person who went through the booth.

Figure 5:
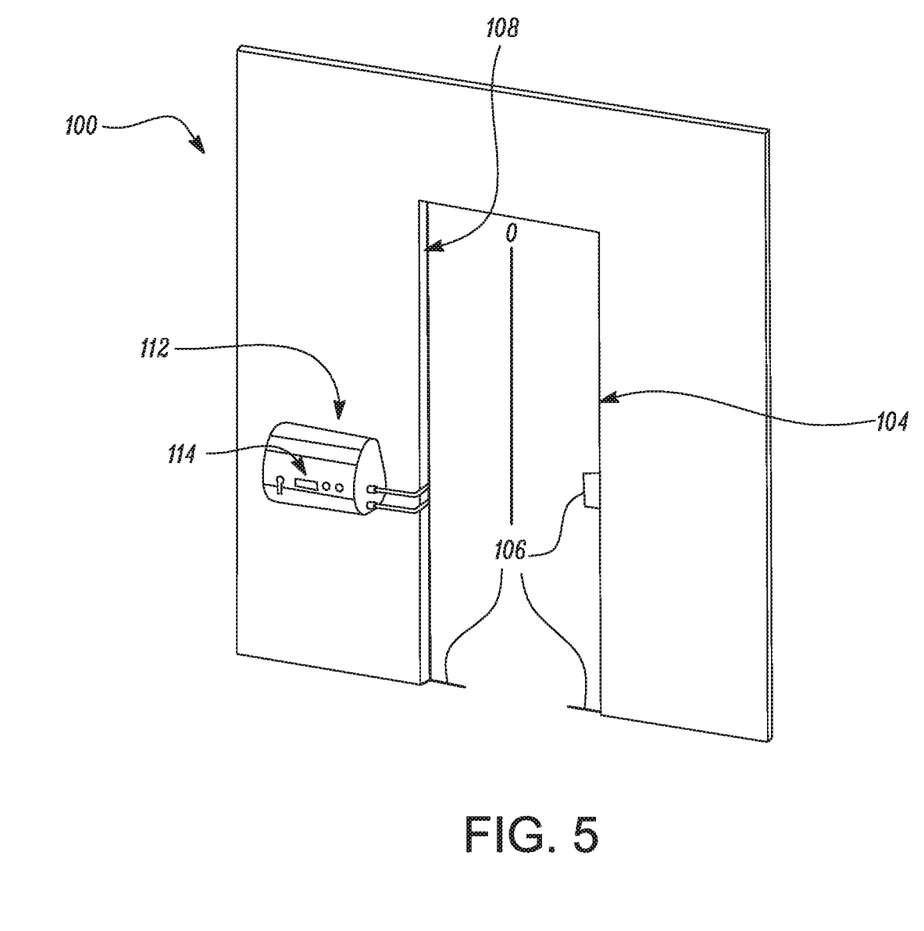
FIG. 5 shows an example of an apparatus of the invention operatively associated with a doorway.

In another example shown in FIG. 5, the apparatus 100, for example for home use, is in the form of a framework 102 shaped and dimensioned similarly to a doorway 104 opening with which it is operatively associated so that a person passing through the doorway may be sanitized. The apparatus 100 includes nozzles 106 located to spray the footwear of the person including soles thereof.

The apparatus 100 is configured to have nozzles 106 located at 5 locations over the extent of liquid reticulation tubing 108 built into the framework 102 so that they spray inwardly onto the person passing through the apparatus 100 from above, the sides, and from below thereby to mist the person almost entirely or entirely.

This example includes a spray nozzle 110 for spraying a parcel or the hands of a person passing through the apparatus 100.

In use, the control box 112 mounted on frame 102 has a start button 114 which is pushed for 10 seconds for person full-body spray or 2 seconds for parcel spray operations.

Figure 6:
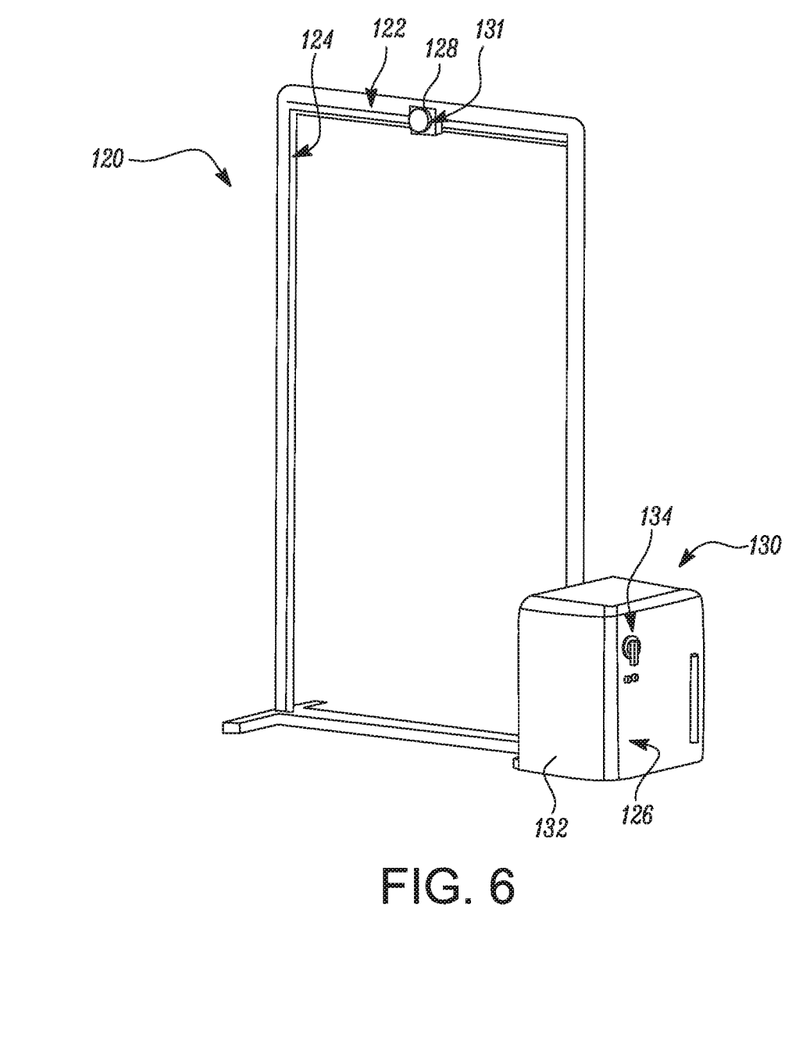
FIG. 6 shows an example of an apparatus of the invention in the form of a doorway like arch.

In the example shown in FIG. 6, the home or office use apparatus 120 of the invention is a self supporting archway in the form of a free standing tubular frame 122 on which a reticulation system 124 is mounted with 8 nozzles for spraying or misting into the archway from the top, bottom and sides. A 25 liter sanitizing fluid tank 130 with a sight glass and sanitizing fluid pumping system 126 provides the pressurized sanitizing fluid for so that the fluid may sprayed from above, laterally, and below the soles of footwear of a person passing therethrough. The pump has an enclosure 132 and an isolation switch 134. The entire enclosure 132 is removable for ease of assembly and disassembly of the apparatus 120.

The apparatus 120 includes a motion sensor 128 and an IR camera 131 for automated operation and symptom detection.

Figure 7:
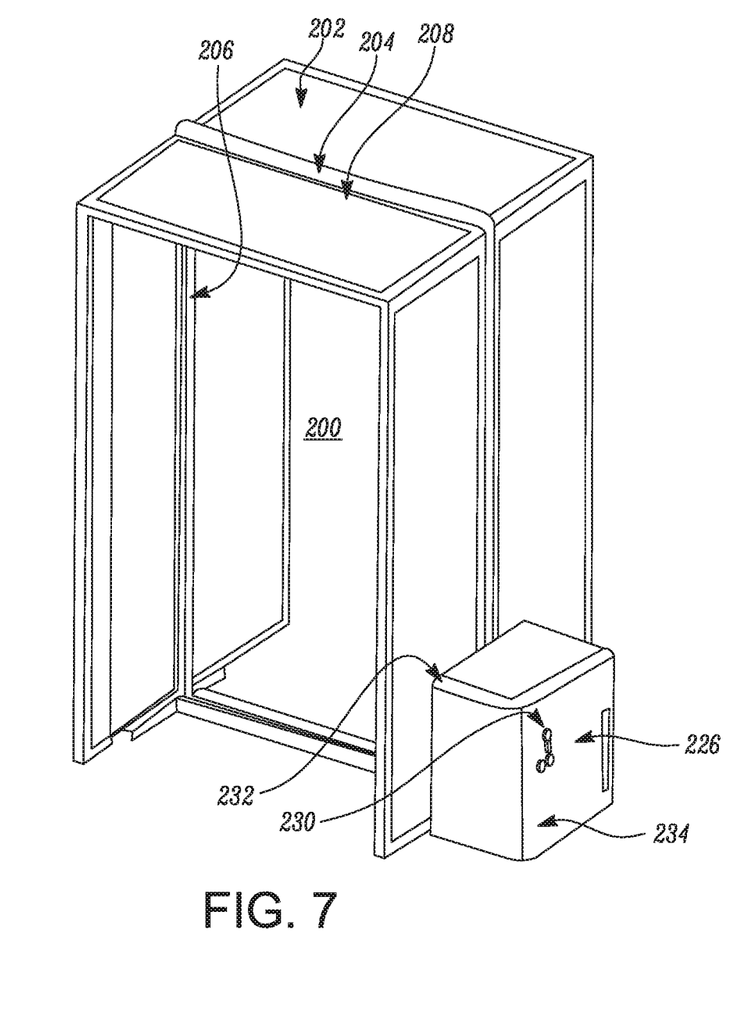
FIG. 7 shows a further example based on the example of FIG. 6, wherein a booth is formed from foldable panels.

FIG. 7 shows an apparatus similar to that of FIG. 6, but converted to make a booth 200 having collapsible and detachable cladded panels 202 attached to a tubular frame 204 as well as piping 206 and 10 nozzles 208 typically holds the IR monitor and camera. As shown for FIG. 6, the nozzles are arranged for spraying or misting into the archway from the top, bottom (soles of shoes) and sides. A 25 liter sanitizing fluid tank 230 with a sight glass and sanitizing fluid pumping system 226 provides the pressurized sanitizing fluid so that the fluid may sprayed from above, laterally, and below the soles of footwear of a person passing therethrough. The pump has an enclosure 232 and an isolation switch 234. The entire enclosure 232 is removable for ease of assembly and disassembly of the booth 200.

Figure 8:
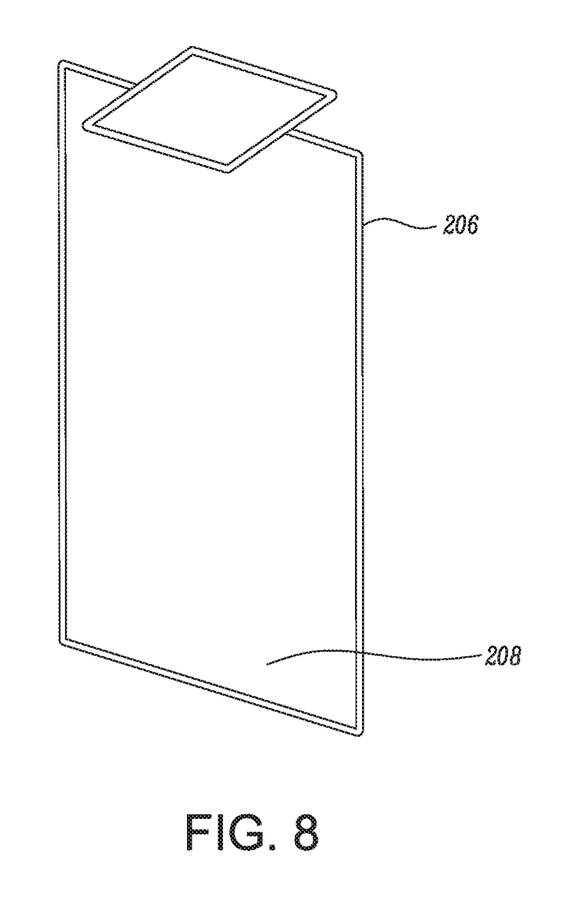
FIG. 8 shows the reticulation system for the booth of FIG. 7.

In FIG. 8 the detail of the enhanced reticulation system of the booth of FIG. 7 over that of the apparatus of FIG. 6 is shown. The reticulation system 206 includes 10 nozzles for spraying or misting into the booth from the top, bottom and sides as well as an additional overhead piping and nozzles ring main and a bottom section 208 including spray nozzles for the soles of shoes.

Figure 9:
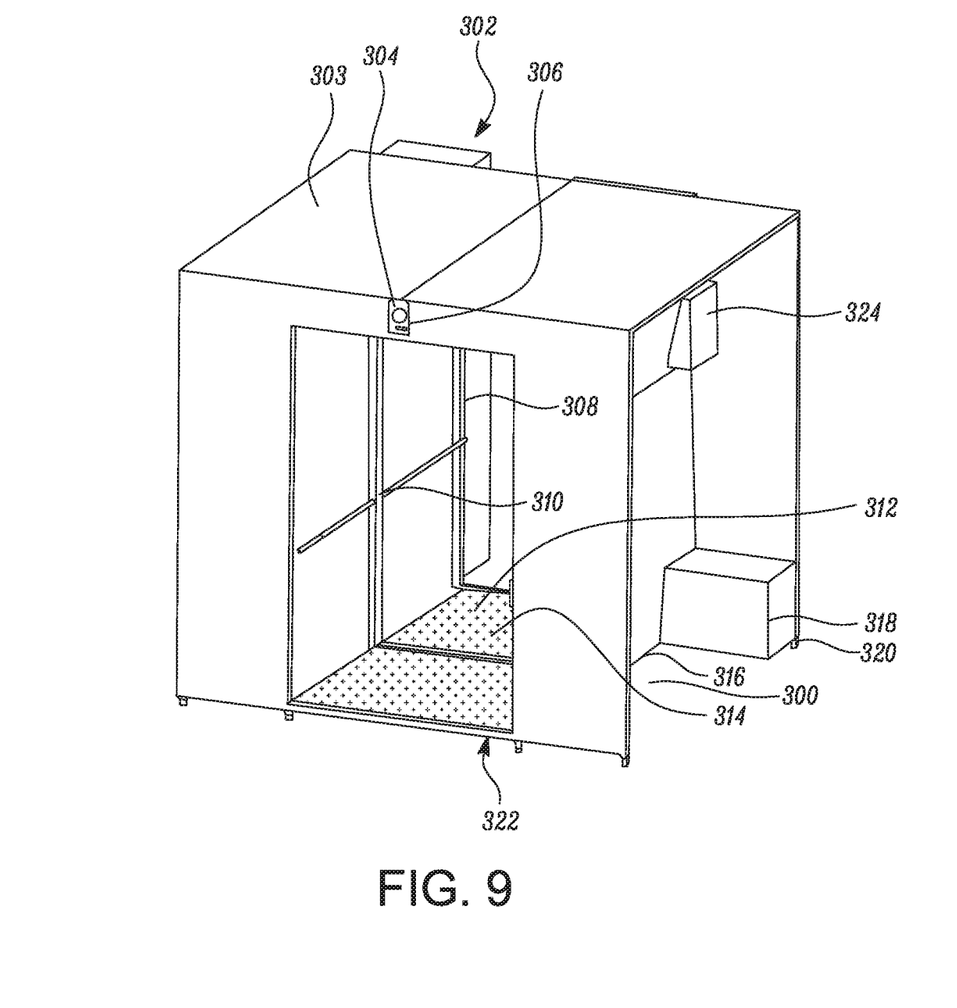
FIG. 9 shows a high-volume booth similar to that of FIGS. 1 to 4 but designed for higher traffic of persons to be sanitized.

FIG. 9 is a high-volume booth similar to that of FIGS. 1 to 4 but designed for higher traffic of persons to be sanitized. This booth 300 is automated and intelligent with a built in 2000 liter tank 302 for long running capacity. The booth 300 is clad with cladding 303, has a motion detector and IR temperature scanner 304 to determine whether a person will be allowed to enter the booth and, if permitted to enter, to initialize sanitization. The user will see indication lights 306 which are green and red.

The booth 300 has a tubular frame 308 and a reticulation system 310 of piping with 16 nozzles for misting from all directions inside the booth 300. The person to be sanitized stands on the grating 312 inside the booth 300 and excess liquid from the misting runs into a drip tray 314 and then out of a drip point 316.

The booth 300 is provided with a pump 318 for the sanitizing liquid from tank 302 and an access ramp 322 into the booth. The booth 300 stands on wheels 320 for easy relocation.

An isolation panel and controls 324 with a programmable controller complete the package.

Figure 10:
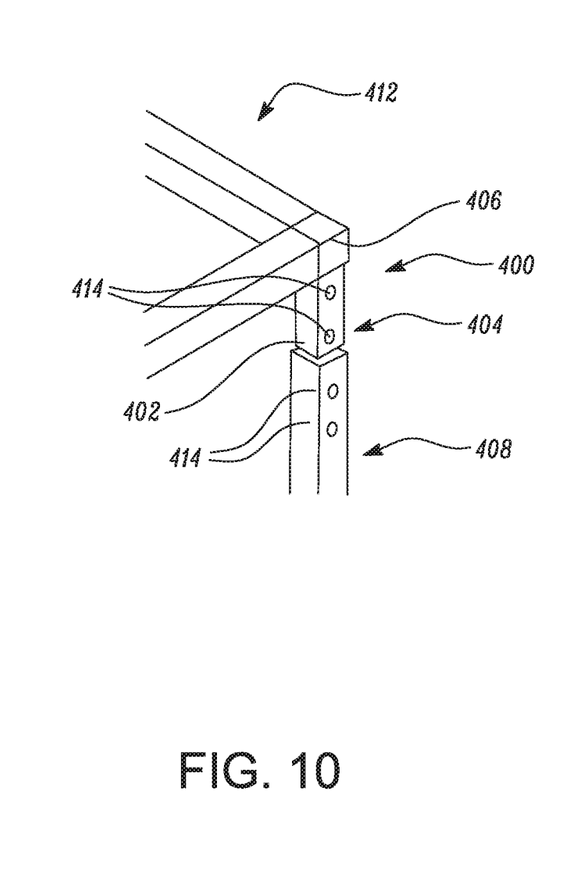
FIG. 10 shows an unassembled corner of a kit for a booth of the invention.
Figure 11:
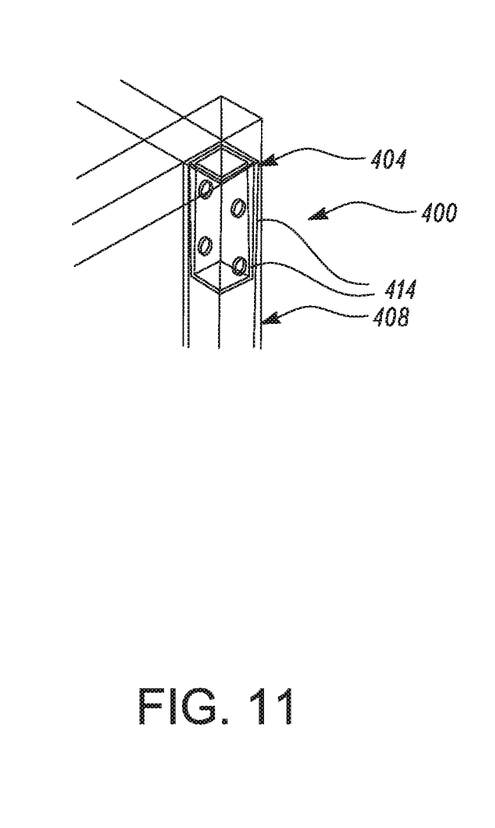
FIG. 11 shows the corner of the kit for a booth of FIG. 10 assembled.
Figure 12:
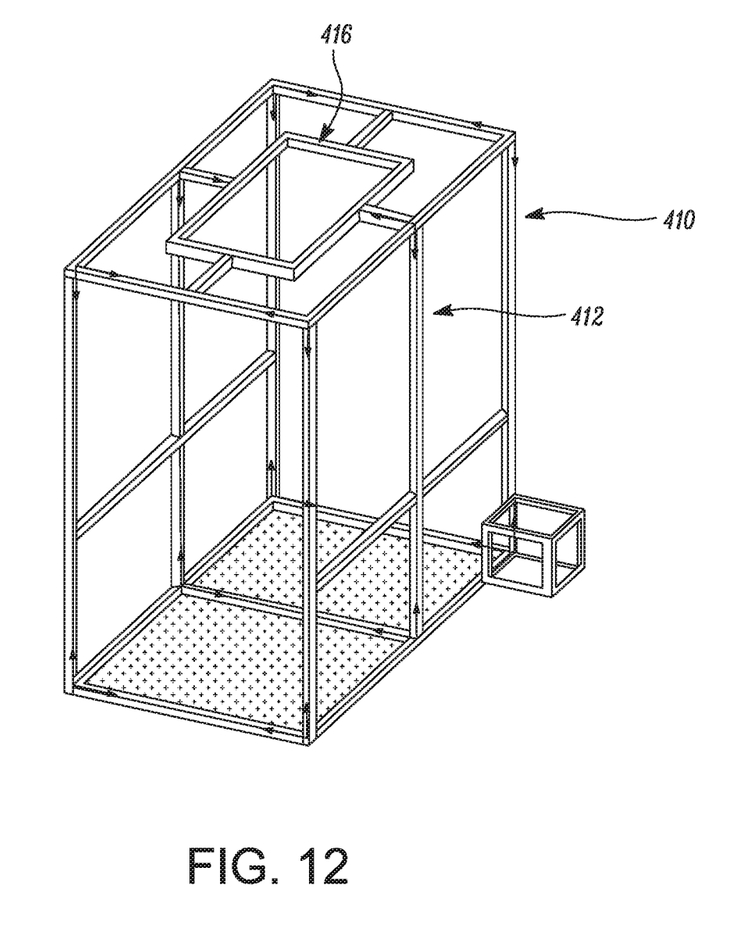
FIG. 12 shows a booth framework assembled from a kit including the corner of FIGS. 10 and 11.

FIGS. 10 to 12 show an example of a kit 400 for assembly of a booth 410 such as that shown in FIGS. 1 to 4, wherein 120 mm length 32 mm×32 mm square tubing 402 is used as a shaft 404 which gets welded onto the 38 mm×38 mm square tubing 406 that makes up the framework 412. A sleeve 408 is made of 38 mm×38 mm square tubing 406 to connect sections of the 32 mm×32 mm shaft 404 to corresponding shafts 404 thereby to assemble the framework 412 of the booth 410. This thus forms a joint as the sleeve 408 slides over the shaft 404 and locks into position using bolts passing through the holes (not shown) and tightening the nuts so that the nuts and bolts are the securing means.

All the shafts 404 and the sleeves 408 have two holes 414 that are pre-drilled that are in register and line up perfectly when the shaft 404 and sleeve 408 are assembled. Once assembled, the booth framework 412 stands firm without the bolts being inserted and nuts tightened.

As can be seen in FIG. 10, the shaft 404 and sleeve 408 are aligned and then the shaft 404 is inserted into the sleeve 408 so that the holes 414 are in register as seen in FIG. 11 and the corner of the booth framework 412 is assembled with only the nuts and bolts being inserted thereafter to secure the parts together.

This assembly procedure applies to all the joints of the framework 412 with the exception of the upper crown portion 416 thereof on some models of the booth 410, as well as the tank and pump stands which may have fully welded joints.

Once assembled all the joints conceal the lug which fits like a hand in a glove with the framework material.

This kit thus allows for quick assemble and ease of dismantling of the booth of the invention.

Still further, the sleeves and shafts are standardized which makes for ease of manufacture, maintenance, and parts supply in the event of any part of the framework being lost or damaged.

FIG. 12 shows, by means of arrows, the assembly of the booth framework from the sleeves and shafts described above and shown in FIGS. 10 and 11.

Advantages of the Invention as Illustrated

The advantages of the invention as illustrated and described are many and include:
  To automatically scan and identify people with a fever or other identifiable symptoms.
  To raise the alarm for such people so that they can be investigated further or be referred to further medical testing.
  To count the number of people and keep a record and statistics of people with high temperature.
  To provide full body disinfecting/sanitizing service of people in seconds including the bottom of their feet up to the top of their heads with little or no human interaction thereby reducing the risk of cross contamination
  To provide a dedicated automated hand sanitizing station
  It is foreseen that the invention will be useful at least for:
1. Healthcare workers before and after their shifts
2. Visitors to hospitals and other health centres (clinics etc.)
3. People in public buildings
4. People everywhere during times of viral outbreaks
5. Public and private office and buildings
6. Food production factories and general industry
7. Ports of entry (land borders, ports, airports)

8. Disinfecting people suspected to have been exposed to a virus (on board a bus, train, aircraft and ships)

What is claimed is:

1. A sanitization apparatus which includes:
a framework which defines a sanitizing zone shaped and dimensioned to permit a person to pass therethrough while being sprayed with sanitizer;
sprayers arranged on the framework for spraying a sanitizer into the sanitizing zone to allow substantial sanitization of an outer surface of a person including clothing, footwear, and soles of the footwear;
a flow communication means for allowing flow communication between the sprayers and a supply of sanitizer via a fluid displacement means; and
a symptom monitoring and access control system, provided for checking persons prior to passing through the sanitization zone, when passing through the sanitization zone, or when exiting the sanitization zone for common symptoms of contagious diseases and for carrying out one or more alert actions when one or more symptoms are identified, preventing the person exhibiting the symptoms from passing through the apparatus, and preventing the person from entering a property until an operator has considered a situation and made a decision.

2. The apparatus as claimed in claim 1, wherein the framework is in the form of a doorway.

3. The apparatus as claimed in claim 2, wherein the framework is free standing.

4. The apparatus as claimed in claim 2, wherein the framework is operatively associated with a door frame so that a person passing through the door frame may be sanitized.

5. The apparatus as claimed in claim 1, wherein the sprayers include nozzles located to spray the footwear of the person including the soles thereof.

6. The apparatus as claimed in claim 1, wherein the sprayers are located over a major portion of the framework so that they spray inwardly onto the person passing through the sanitizing zone from above, sides, and from below, thereby to allow a mist of sanitizer to be deposited onto the outer surface of said person.

7. The apparatus as claimed in claim 1, wherein the framework is in the form of a booth having an entrance and an exit, whereby a person enters into the booth, remains in the booth to be sprayed, and then exits the booth, wherein the booth includes a hand sanitization portion which is arranged in flow communication with the supply of sanitizer and which is located at the entrance, or the exit, of the booth so as to facilitate sanitization of said person's hands which may have been used to cover their eyes while in the booth.

8. The apparatus as claimed in claim 1, wherein the apparatus has two or more side walls and a substantially perforated floor for allowing a sanitizer mist sprayed toward the person from below to pass through the floor to sanitize the soles of the footwear of the person, while also permitting drainage of sprayed sanitizer of a booth.

9. The apparatus as claimed in claim 8, wherein the floor is made of grating having a drip tray to contain any contaminated sanitizer after use.

10. The apparatus as claimed in claim 8, wherein the side walls and roof are made of one or more webbing materials selected from the group including canvas, nylon, and polyester, and a metal sheeting made from a metal selected from the group including galvanized steel and stainless steel.

11. The apparatus as claimed in claim 1, wherein the communication means is in the form of a liquid reticulation system which includes an intermediate zone for spraying a side of a person passing through the sanitization zone, a portion of the intermediate zone of the liquid reticulation system extending parallel to a direction of passage of a person passing through the sanitization zone.

12. The apparatus as claimed in claim 1, wherein the communication means is in the form of a liquid reticulation system which includes an upper zone for spraying a person passing through the sanitization zone from above, the upper zone extending around a periphery of an upper portion of the framework so that the spray is directed at the person directly from above as well as angularly from above, wherein the upper zone of the liquid reticulation system is C-shaped, O-shaped, or rectangular in plane view configuration.

13. The apparatus as claimed in claim 1, wherein the communication means is in the form of a liquid reticulation system which includes a lower zone for spraying a person passing though the sanitization zone from below, the lower zone of the liquid reticulation system extending in an orientation selected from transversely and longitudinally oriented to a floor of the framework, and wherein the lower zone of the liquid reticulation system extends around a periphery of a lower portion of the framework so that the spray is directed upwardly at the person as well as angularly from below to improve coverage by the sanitizer being sprayed onto the footwear and lower extremities of the person within the sanitization zone.

14. The apparatus as claimed in claim 1, wherein the supply of sanitizer includes a liquid container for the sanitizer, and a container support portion whereby the liquid container is in a predetermined position relative to the orientation of the apparatus; and
the fluid displacement means in the form of a pump is located on the framework in flow communication with an outlet of the container, an outlet of the pump being connected to the communication means in the form of a liquid reticulation system to supply the liquid reticulation system with pressurized liquid sanitizer from the container.

15. The apparatus as claimed in claim 14, wherein the pump is in the form of a dosing pump for allowing a pre-determinable quantity of sanitizer to be sprayed onto a person, to thereby permit monitoring of a safe usage rate and consumption of the sanitizer.

16. The apparatus as claimed in claim 1, wherein the apparatus includes a consumption monitoring means for monitoring consumption of the sanitizer so as to allow a pre-determinable quantity of sanitizer to be sprayed onto a person, wherein the consumption monitoring means is selected from the group including a flow meter whereby the amount of sanitizer passing through the nozzles is recorded for control purposes, and level monitor whereby the change in level of the sanitizer is monitored and recorded.

17. The sanitization apparatus as claimed in claim 1, wherein the symptom monitoring system includes a body temperature measurement system which either presents the temperature of the person to an operator or, through pre-programmed software, alerts when a person's temperature is outside predetermined parameters.

18. The sanitization apparatus as claimed in claim 17, wherein the symptom monitoring system includes a camera and software pre-programmed to identify common symptoms from a camera image whereby, when symptoms are identified from the camera image, the operator is alerted or the alarm may be activated, where symptoms include one or more symptoms selected from the group of symptoms identifiable from the eyes, skin color, sweat, coughing, temperature, and facial expression of a person.

* * * * *